(12) United States Patent
Peng et al.

(10) Patent No.: US 9,108,949 B2
(45) Date of Patent: Aug. 18, 2015

(54) COMPOUNDS AND METHODS OF PROPHYLAXIS AND TREATMENT REGARDING NICOTINIC RECEPTOR ANTAGONISTS

(75) Inventors: Youyi Peng, New York, NY (US); Lawrence P. Wennogle, New York, NY (US); Qiang Zhang, New York, NY (US); John Tomesch, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 14/127,699

(22) PCT Filed: Jun. 22, 2012

(86) PCT No.: PCT/US2012/043813
§ 371 (c)(1),
(2), (4) Date: Mar. 27, 2014

(87) PCT Pub. No.: WO2012/178057
PCT Pub. Date: Dec. 27, 2012

(65) Prior Publication Data
US 2014/0205595 A1    Jul. 24, 2014

Related U.S. Application Data

(60) Provisional application No. 61/501,207, filed on Jun. 25, 2011.

(51) Int. Cl.
| | | |
|---|---|---|
| *A61K 31/445* | (2006.01) | |
| *C07D 401/12* | (2006.01) | |
| *A61K 31/454* | (2006.01) | |
| *A61K 45/06* | (2006.01) | |
| *A61K 31/4745* | (2006.01) | |
| *A61K 31/7068* | (2006.01) | |
| *A61K 33/24* | (2006.01) | |

(52) U.S. Cl.
CPC ............ *C07D 401/12* (2013.01); *A61K 31/454* (2013.01); *A61K 31/4745* (2013.01); *A61K 31/7068* (2013.01); *A61K 33/24* (2013.01); *A61K 45/06* (2013.01)

(58) Field of Classification Search
USPC ............................................ 514/326, 49, 283
See application file for complete search history.

(56) References Cited

U.S. PATENT DOCUMENTS

| | | | |
|---|---|---|---|
| 7,799,782 B2 * | 9/2010 | Munson et al. ............ | 514/234.5 |
| 2004/0220170 A1 * | 11/2004 | Atkinson et al. ........... | 514/210.2 |
| 2010/0179186 A1 | 7/2010 | Papke et al. | |

FOREIGN PATENT DOCUMENTS

WO    WO 2009/112459 A1    7/2010

OTHER PUBLICATIONS

Peng et al., Bioorganic & Medicinal Chemistry Letters, 2010, 20:4825-4830.*
Atkinson et al. CAS: 141:395577, 2004.*
Lukas, R. J. et al, *Pharmacol. Rev.*, 51, 397-401 (1999).
Flores, C. et al., *Mol. Pharmacol.*, 41, 31-37 (1992).
Lindstrom J. et al, *Prog. Brain Res.*, 109, 125-137 (1996).
Arneric, S.P. et al, *Biochem. Pharmacol.*, 74, 1092-1101 (2007).
Mazurov A. et al, *Curr. Med. Chem.*, 13, 1567-1584 (2006).
Olincy A., *Arch. Gen. Psychiatry*, 63, 630-638 (2006).
Chang, C. C, et al. *J. Biomed. Sci.*, 6, 368-375 (1999).
Davies, A. R., et al., *Neuropharmacology*, 38, 679-690 (1999).
Jensen, A. A., et. al. *J. Med. Chem.*, 48, 4705-4745 (2005).
Sciamanna, *J. Neurochem.* 69, 2302-2311 (1997).
Paleari, et al. *Int. J. Cancer.* 125, 199-211 (2009).
Buckingham et al, *Pharmacological Reviews*, vol. 61 No. 1, 39-61 (2009).
Jones, et al, *J Mol Neurosci.*, 30 (1-2):83-84 (2006).
Roncarati, *J Pharmacol Exp Ther.*, 329(2):459-468. (May 2009, Epub Feb. 17, 2009).
Papke, et al., Journal of Pharmacology and Experimental Therapeutics, vol. 329 No. 2 791-807 (2009).
Peng, et al., "Discovery of Novel alpha7 Nicotinic Receptor Antagonists", *Bioorganic & Medicinal Chemistry Letters* 20, pp. 4825-4830 (2010).
Henchman, et al., "Ligand-Induced Conformational Change in the alpha7 Nicotinic Receptor Ligand Binding Domain", *Biophysical Journal*, vol. 88(4), pp. 2564-2576 (2005).

* cited by examiner

*Primary Examiner* — Rei-Tsang Shiao
(74) *Attorney, Agent, or Firm* — Hoxie & Associates LLC

(57) ABSTRACT

It is an object of the present invention that the novel nicotinic receptor antagonists disclosed herein may be used in a broad array of clinical or medicinal facets. For example, it is a contemplated use of the present invention that the novel nicotinic receptor antagonists be used to inhibit the growth cycle of non-small cell lung cancer cells. Without being bound by theory, it is an object of the present invention that the nicotinic receptor antagonists disclosed herein are believed to possess reversible binding properties. Moreover, the compounds of the present invention are selective for 0.7 nAChR. For example, the compounds of the present invention are not believed to bind to 0.4 (32 nAChR neuromuscular receptors. It is also contemplated that the nicotinic receptor antagonists of the present invention will be used as a counter measure to treat exposure, or potential exposure, to a wide array of potential neurotoxins.

16 Claims, 9 Drawing Sheets

COMPOUNDS AND METHODS OF PROPHYLAXIS AND TREATMENT REGARDING NICOTINIC RECEPTOR ANTAGONISTS

STATEMENT REGARDING GOVERNMENT FUNDING

This invention was made, in part, with government support under Grants No. R43 MH067488-01 and R01 GM57484 awarded by the National Institutes of Health, and Grants No. DAMD 17-03-2-0019 and W81XWH-06-C-0013 awarded by the United States Army Medical Research and Material Command NETRP. The government has certain rights in the invention.

CROSS REFERENCE TO RELATED APPLICATIONS

This application is a national stage application under 35 U.S.C. §371 of PCT/US2012/043813, filed on Jun. 22, 2012, which claims the benefit of PCT/US2011/041866 filed Jun. 24, 2011 and U.S. Provisional Application No. 61/501,207 filed, Jun. 25, 2011, the contents of each of which are incorporated herein by reference in their entireties.

TECHNICAL FIELD

The field generally relates to organic compounds that act as nicotinic receptor antagonists. The field further relates to the use of nicotinic receptor antagonists for use as a prophylaxis and/or treatment for both small and non-small cell lung cancer, HIV, cognitive disorders, Alzheimer's disease, smoking cessation, Schizophrenia, and mammalian exposure to various neurological toxins.

BACKGROUND OF THE INVENTION

Nicotinic acetylcholine receptors (nAChRs) belong to the Cys-loop subfamily of pentameric ligand-gated ion channels and can be classified into muscle-type and neuronal subtypes. The neuronal nAChRs comprise twelve subunits ($\alpha 2$-$\alpha 10$ and $\beta 2$-$\beta 4$) with different arrangements, while the muscle-type is consisted of four subunits in a single arrangement of $\alpha 1\gamma\alpha 1\beta 1\delta$ ($\gamma$ is replaced by $\epsilon$ in the adult). (Lukas, R. J. et al., *Pharmacol. Rev.* 1999, 51, 397) Two major neuronal receptors $\alpha 4\beta 2$ and $\alpha 7$ have been identified in the central nervous system. (Flores, C. et al., *Mol. Pharmacol.* 1992, 41, 31; Lindstrom J. et al., *Prog. Brain Res.* 1996, 109, 125) The neuronal $\alpha 7$ nAChR has been proposed as a potential therapeutic target for a broad range of neurodegenerative and psychiatric diseases, including Alzheimer's disease, schizophrenia, anxiety, and epilepsy. A variety of selective partial and full agonists have been developed for the $\alpha 7$ nAChR as potential therapeutics. (Jensen A. et al., *Prog., Brain Res.* 1996) Several $\alpha 7$ nAChR selective agonists (e.g., TC-5619 and MEM-3454) have advanced to clinical trials for Alzheimer's disease and schizophrenia. (Arneric, S. P. et al., *Biochem. Pharmacol.* 2007, 74, 1092; Mazurov A. et al., *Curr. Med. Chem.* 2006, 13, 1567; Olincy A., *Arch. Gen. Psychiatry* 2006, 63, 630) Although extensive efforts have been taken to identify selective $\alpha 7$ nAChR agonists, the development of $\alpha 7$ selective antagonists is relatively limited. Some studies have reported that certain naturally derived compounds may be incorporated as $\alpha 7$ selective antagonists. For example, the krait *Bungarus multicinctus* derived peptide toxin α-bungarotoxin (α-BTX) and the seeds of Delphinum isolated nonpetide toxin methyllycaconitine (MLA) are two frequently used $\alpha 7$ selective antagonists. (Chang, C. C., et al. *J. Biomed. Sci.* 1999, 6, 368; Davies, A. R., et al. *Neuropharmacology* 1999, 38, 679)

Unfortunately, α-BTX is a potent antagonist for muscle-type nAChRs as well, and both compounds also inhibit nAChR subtypes $\alpha 9$ and $\alpha 9\alpha 10$. (Jensen, A. A., et. al. *J. Med. Chem.* 2005, 48, 4705) Nevertheless, subtype-selective antagonists may possess intrinsic value as tools to define the roles played by $\alpha 7$ nAChRs in the physiological and pathophysiological processes.

Indeed, and along these same lines, nicotinic acetylcholine receptors have been implicated as possible drug targets in a myriad of various disease states and for use as a possible measure for counter-terrorism purposes.

For example, with regards to various disease states, nAChRs have for some time now been studied in an attempt to find a possible nexus between targeting of the receptor and treatment of small cell lung carcinoma (SCLC). (Sciamanna, *J. Neurochem.* 69, 2302-2311 1997). While SCLC is a neuroendocrine neoplasm that accounts for a minority of newly diagnosed lung cancers, roughly a quarter, it is quite deadly and patients generally die within a mere year of being diagnosed. Thus, there is a pertinent need for the development of treatments, or means of prophylaxis, that can be administered to a patient in order to mitigate, or achieve complete ablation of, the SCLC disease state.

Despite the attendant need, few, if any, specific treatments are available for SCLC. However, the most current data available in the field indicates that two types of nAChRs can regulate NA and CA influx. Such regulation of calcium and sodium influx has biological and therapeutic ramifications in the treatment of neuroendocrine neoplasms. Thus, in light of the paucity of compounds available that can effectively and specifically target such channels, there still remains a glaring need for rationally based compounds that have the ability to target such receptors.

In addition to developing a more efficacious means for treating SCLC, there is also an attendant need for compounds that may be used to treat the more widespread dilemma of non-small cell lung cancer (NSCLC). In this regard it has been observed that mesothelioma and non-small cell lung cancer express functional nAChR. (Paleari, et al. *Int. J. Cancer:* 125, 199-211 2009) Thus, there has been speculation that nicotine may play some heretofore-unknown role in contributing to lung cancer pathogenesis via activation of such cellular proliferation pathways as Akt signaling or by inhibiting other natural cellular apoptotic machinery. (Id) However, some studies have indicated that nicotine acts on nAChRs, expressed in NSCLC tumor cells, by activating a proliferative response in such cells. (Id)

Next, despite their distinct disease pathology, it has been discovered that disease states such as cancer and AIDS have a common link via nAChRs. In addition to the need to develop treatments for both small and non-small cell lung cancer, however, there is also a need for compounds or treatment mechanisms that have the ability to effectively combat HIV and AIDS, disease states that also pose a very serious threat to public health worldwide. In fact more than 40 million people are infected worldwide with HIV-1 and an estimated 14,000 new infections occur every day. Since the first cases of AIDS were identified in 1981 the deaths of over 25 million people have been attributed to HIV/AIDS.

As mentioned, alpha-7 nAChRs has been found in lung cancer cells where activation by either natural molecules or compounds in tobacco smoke are shown to promote cancer growth. It has been found that those same alpha-7 nAChRs are upregulated in immune cells in AIDS. This suggests that over activation of alpha-7 receptors in macrophages by the AIDS virus protein, may cause premature cell death. Thus, and at the very least, antagonists to nAChRs are needed to continue to exploit the relationship between cancer, AIDS and nAChR activity, and thus provide treatments for these disease states.

Additionally, nicotinic acetylcholine receptors have been also been implicated to play a role in neurodegenerative diseases and cognitive disease or disorders. For example, nicotinic acetylcholine receptors have been implicated in disease such as Alzheimer's disease. Buckingham et al., *Pharmacological Reviews* March 2009 vol. 61 no. 1 39-61. Moreover, α7 nAChR have specifically been identified as playing a some type of role in the etiology and/or pathology of Alzheimer's disease. Jones I W, et al., J Mol *Neurosci*. 2006; 30 (1-2):83-4.

Nicotinic acetylcholine receptors have been also been suggested to play a role in certain neurodegenerative and cognitive disorders. The alpha7 nicotinic acetylcholine receptor (nAChR) has been thought of as a target for treatment of cognitive dysfunction associated with Alzheimer's disease and schizophrenia. J Pharmacol Exp Ther, 2009 May; 329(2): 459-68. Epub 2009 Feb. 17.

However, despite these suggested links to a number of disparate diseases and disorders, there are attendant issues with nicotinic acetylcholine receptors. For example nicotinic acetylcholine receptors represent a comp ex and diverse set of receptor subtypes. Additionally, prolonged use may lead to desensitization of the receptor. Papke, et al., *Journal of Pharmacology and Experimental Therapeutics*, May 2009 vol. 329 no. 2 791-807.

These latter factors have made it difficult to work with nicotinic acetylcholine receptors and to develop compounds that are efficacious both in the short and long term.

SUMMARY OF THE INVENTION

It is an object of the present invention that the novel nicotinic receptor antagonists disclosed herein may be used in a broad array of clinical or medicinal facets. For example, it is a contemplated use of the present invention that the novel nicotinic receptor antagonists be used to inhibit the growth cycle of non-small cell lung cancer cells.

Without being bound by theory, it is an object of the present invention that the nicotinic receptor antagonists disclosed herein are believed to possess reversible binding properties. Moreover, the compounds of the present invention are selective for α7 nAChR. For example, the compounds of the present invention are not believed to bind to α4β2 nAChR neuromuscular receptors.

It is also contemplated that the nicotinic receptor antagonists of the present invention will be used as a counter measure to treat exposure, or potential exposure, to a wide array of potential neurotoxins. The AChRs are activated by acetylcholine (ACh), which is hydrolyzed to choline by acetylcholineesterase (AChE). When AChE is irreversibly inhibited by organophosphorus nerve agents like DFP and sarin, the uncontrolled accumulation of ACh at peripheral and central muscarinic AChRs (mAChRs) and nAChRs causes the cholinergic syndrome. This syndrome is characterized by sweating, pupillary constriction, convulsions, tachycardia, and eventually death.

The currently acknowledged treatment for nerve agent intoxication is the mAChR antagonist atropine used in concert with an oxime reactivator of AChE (e.g., pralidoxime). However, while this treatment regimen does not directly target nicotinic receptors both mAChRs and nAChRs are involved in nerve agent toxicity. It has been shown that, for example, nAChR antagonists 1i and 2, when tested in a DFP toxicity animal model to investigate their anti-seizure activity, (Peng et al.; Racine, R. J. *Electroencephalogr. Clin. Neurophysiol*. 1972, 32, 269.) that pretreatment with compounds 1i and 2 antagonized DFP-induced seizure-like behaviors over a 2 h period post-injection by 93.4% and 91.2%, respectively. These results suggest that the compounds of the present invention could provide neuroprotection against seizure-like behaviors induced by DFP and, therefore, may be useful for treatment of organophosphus nerve agent intoxication. Moreover, it is also contemplated that the compounds disclosed herein provide a means of discerning between the physiological roles of neuronal α7 nAChR under normal and diseased states, and as diagnostic tools used for discovering potential therapies for organophosphorus nerve agent intoxication.

As well, it is also contemplated that the nicotinic receptor antagonists of the present invention could be used as means for prophylaxis or treatment of HIV and/or AIDS. In a preferred aspect, novel α7 nAChR selective antagonists are administered in an effective therapeutic dose causing some measure of reduced symptomology or total ablation of the disease state.

However, while not bound by any theory, it is also believed that while the compounds of the present invention are selective α7 nAChR antagonists, that this does not also mean that the compounds activity is overall anticholinergic. Again, while not bound by any theory, it is surprising that these selective antagonists enhance cognition. Without being bound by theory, it is theorized that at lower doses or over extended periods, that the compounds disclosed herein may reduce desensitization in response to acetylcholine, which thereby enhances the effects of endogenous acetylcholine.

In yet another aspect of the present invention the novel nicotinic receptor antagonists disclosed herein could be used to have a protective effect on patients in order to prevent sepsis.

In still another aspect of the present invention the novel nicotinic receptor antagonists disclosed herein could be used, either alone or combination with another pharmaceutical, to treat Alzheimer's disease. It is contemplated that the present invention may also treat the symptoms of Alzheimer's disease. In one aspect it is contemplated the present invention may be used to treat at least one symptom of Alzheimer's disease.

It is contemplated by the present invention that the nicotinic receptor antagonists disclosed herein may also treat at least one symptom of Alzheimer's disease wherein that symptom of Alzheimer's disease relates to cognitive impairment.

In another aspect of the present invention it is contemplated that the novel nicotinic receptor antagonists disclosed herein could be used to treat or prevent relapse of opioid, cocaine, nicotine, and methamphetamine use. For example, it is contemplated that the novel nicotinic receptor antagonists disclosed herein could be used to in treatments directed toward smoking cessation.

In yet anther aspect, it is contemplated that the novel nicotinic receptor antagonists disclosed herein could be used to treat and/or improve cognition and/or cognition related diseases or disorders.

It is further contemplated that the compounds of the present invention may be used to treat dementia. In one embodiment the compounds of the present invention may be used to treat psychosis, e.g., in schizophrenia, schizoaffective disorder, schizophreniform disorder, psychotic disorder, delusional disorder, mania or bipolar disorder.

It is also contemplated that the compounds of the present invention may be used to treat cognitive impairment wherein cognitive impairment is a result and/or symptom of psychosis, e.g., in schizophrenia, schizoaffective disorder, schizophreniform disorder, psychotic disorder, delusional disorder, mania or bipolar disorder.

In another aspect of the present invention, it is further contemplated that novel α7 nAChR selective antagonists may be used as research or diagnostic tools. It is further contemplated that novel α7 nAChR selective antagonists could be used as a research tool in elucidating signal transduction in neuronal tissue. It is also contemplated that novel α7 nAChR selective antagonists could be used as a research tool in elucidating signal transduction pathway in non-neuronal tissue as well.

It is further contemplated that the compounds disclosed herein may be used to treat cognitive impairment that is the symptom of a medication used to treat cognitive related disease/disorder, e.g., Alzheimer's disease, schizophrenia.

DETAILED DESCRIPTION OF THE INVENTION

Figure 1:
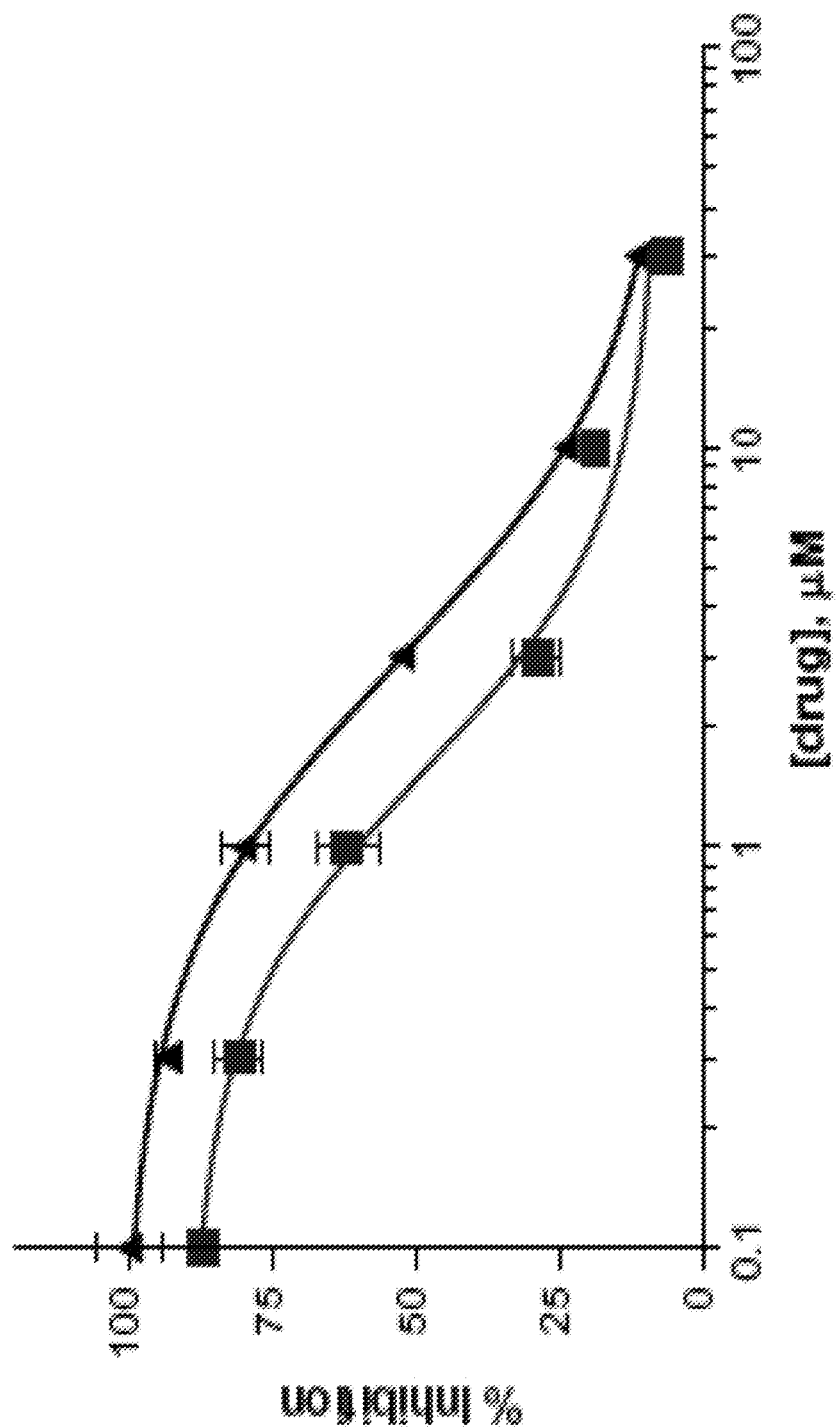
FIG. 1 is a depiction of a representative dose response curves of Compound 1 and Compound 2 on the native neuronal alpha-7 nAChR in rat brain membranes.

The examples provided in the detailed description are merely examples, which should not be used to limit the scope of the claims in any claim construction or interpretation.

The present invention contemplates nicotinic acetylcholine receptor antagonists of Formula I:

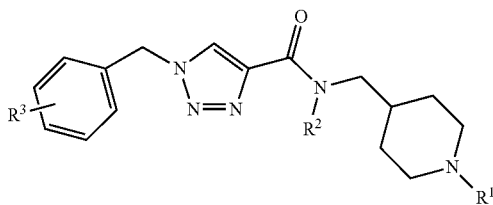

Wherein $R_1$ may be a benzyl, phenethyl, 2-methoxyethyl, isobutyl, or cyclopentyl group.
Wherein $R_2$ may be a hydrogen or methyl group.
Wherein $R_3$ may be a chlorine, methoxyethyl, methyl, flourine or cyclopentyl group.

The present invention contemplates nicotinic acetylcholine receptor antagonists of Formula II:

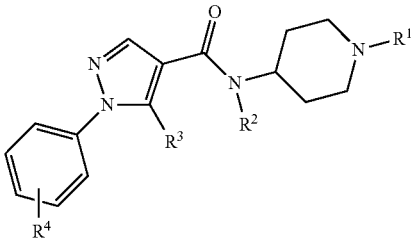

Wherein $R_1$ may be a benzyl, methyl, or hydrogen group
Wherein $R_2$ may be H or methyl.
Wherein $R_3$ may be a propyl, methyl, cyclopropyl, and 4-tolyl group.
Wherein $R_4$ may be a hydrogen, fluorine, chlorine or furyl group.

The treatment of patients with the novel α7 nAChR selective ligands as described above addresses the immediate, and increasing, need for safer and more efficacious compounds to treat patients who suffer from diseases or disorders correlated with the activation of the nicotinic acetylcholine receptors pathways associated with the aforementioned disease states.

Accordingly, the present invention provides Method I for the treatment or prophylaxis of a disease or disorder characterized by the activation of an acetylcholine receptor pathway, comprising administering to the patient an effective amount of a α7 nicotinic acetylcholine receptor antagonists according to Formula I or Formula II in a free or pharmaceutically acceptable salt form, for example:

1.1 Method I, wherein said disease or disorder is small cell lung cancer.
1.2 Method I wherein said disease or disorder is non-small cell lung cancer.
1.3 Method I, wherein said disease or disorder is organophosphorus nerve agent intoxication
1.4 Method I, wherein said disease or disorder is infection via the human immunodeficiency virus (HIV).
1.5 Method I, wherein said disease or disorder is the result of autoimmune deficiency syndrome (AIDS).
1.6 Method I, or any of methods 1.1-1.5, wherein the patient is a human.
1.7 Method I, or any of methods 1.1-1.2, wherein the disease or disorder is characterized by metastatic cancerous cells.
1.8 Method I, or any of methods 1.1-1.2, wherein the disease or disorder is characterized by benign cancerous cells.
1.9 Method I, or any of methods 1.1-1.2, 1.7, 1.8, wherein said disease or disorder characterized by the presence of cancerous cells may be selected from the following group of diseases or disorders: squamous cell carcinoma, adenocarcinoma, large cell carcinoma, and pleuroa mesothelioma.
1.10 Method I, or any of methods 1.1-1.2, 1.7-1.9, wherein said disease or disorder is a solid tumor carcimona.
1.11 Method I, or any of methods 1.1-1.2, 1.7-1.10, wherein a patient is suffering from or at risk for developing cancer.
1.12 Method I, or any of methods 1.1-1.2, 1.7-1.10, wherein a novel α7 nicotinic acetylcholine receptor antagonist of Formula I is administered simultaneously with a second treatment for cancer selected from the group consisting of: capecitabine, trastuzumab, pertuzumab, cisplatin and irinotecan.
1.13 Method I, wherein the disease or disorder is a cognitive impairment and/or a disease or disorder related to cognitive impairment.

1.14 Method I or 1.13, wherein the cognitive related disease or disorder is mild cognitive impairment
1.15 Method I or 1.13-1.14, wherein the α7 nicotinic acetylcholine receptor antagonists according to Formula I or Formula II are used to treat at least one of the symptoms of cognitive impairment, e.g. impaired auditory processing and attention, impaired spatial organization, impaired verbal learning, impaired semantic and verbal memory, impaired executive functions.
1.16 Method I or any of 1.13-1.15 wherein the disease or disorder is Alzheimer's disease.
1.17 Method I or any of 1.13-1.16, wherein the effective amount of an α7 nicotinic acetylcholine receptor antagonist is used to treat at least one symptom of Alzheimer's disease.
1.18 Method I or 1.17, wherein the symptom of Alzheimer's disease is cognitive impairment, e.g., impaired auditory processing and attention, impaired spatial organization, impaired verbal learning, impaired semantic and verbal memory, impaired executive functions.
1.19 Method I, wherein the treatment is directed toward smoking cessation in a patient.
1.20 Method I or any of methods 1.13-1.15 wherein the α7 nicotinic acetylcholine receptor antagonist is used to treat psychosis, e.g., in schizophrenia, schizoaffective disorder, schizophreniform disorder, psychotic disorder, delusional disorder, mania or bipolar disorder.
1.21 Method I, or 1.20 wherein cognitive impairment is any of the following, e.g., impaired auditory processing and attention, impaired spatial organization, impaired verbal learning, impaired semantic and verbal memory, impaired executive functions.
1.22 Method I, or 1.20, 1.21, wherein the cognitive impairment is a symptom of the psychosis, e.g., schizophrenia, schizoaffective disorder, schizophreniform disorder, psychotic disorder, delusional disorder, mania or bipolar disorder.
1.23 Method I or any of the preceding methods wherein the patient is administered an effective amount of an α7 nicotinic acetylcholine receptor antagonist according to Formula I.
1.24 Method I or any of the preceding methods wherein the patient is administered an effective amount of an α7 nicotinic acetylcholine receptor antagonist according to Formula II.
1.25 Method I, or any the preceding methods, wherein a patient is administered an effective amount of a novel α7 nicotinic acetylcholine receptor antagonist of Formula I in a pharmaceutically acceptable carrier.
1.26 Method I, or any of the preceding methods, wherein administration of an effective amount of an novel α7 nicotinic acetylcholine receptor antagonist of Formula I or II improves cognition.
1.27 Method I, or any of the preceeding methods, wherein the administration of an effective amount of an novel α7 nicotinic acetylcholine receptor antagonist of Formula I or II is used to treat Alzheimer's disease and/or a symptom of Alzheimer's disease.
1.28 Method I, or any of the preceeding methods, wherein the administration of an effective amount of an novel α7 nicotinic acetylcholine receptor antagonist of Formula I or II is used to treat schizophrenia and/or a symptom of schizophrenia.
1.29 A pharmaceutical composition comprising a compound according to claim 1 or 2 in admixture with a pharmaceutically acceptable diluent or carrier.

In accordance with this detailed description, the following abbreviations and definitions apply. It must be noted that as used herein, the singular forms "a", "and", and "the" include plural referents unless the context clearly dictates otherwise. Thus, for example, reference to "a compound" includes a plurality of such compounds and reference to "the dosage" includes reference to one or more dosages and equivalents thereof known to those skilled in the art, and so forth.

The term "treating", "treatment", and the like are used herein to generally mean obtaining a desired pharmacological and physiological effect. The novel α7 nAChRs described herein which are used to treat a subject with cancer generally are provided in a therapeutically effective amount to achieve any one or more of the following inhibited tumor growth, reduction in tumor mass, loss of metastatic lesions, inhibited development of new metastatic lesions after treatment has started, or reduction in tumor such that there is no detectable disease (as assessed by, e.g., radiologic imaging, biological fluid analysis, cytogenetics, fluorescence in situ hybridization, immunocytochemistry, colony assays, multiparameter flow cytometry, or polymerase chain reaction). The term "treatment", as used herein, covers any treatment of a disease in any mammal, particularly a human, known to those that are skilled in the art The term "subject" or "patient" as used herein is meant to include a mammal. In a preferred aspect of the present invention the mammal is a human. In another preferred aspect of the present invention the mammal is a domestic animal.

The term "pharmaceutically effective" as used herein refers to the effectiveness of a particular treatment regime. Pharmaceutical efficacy can be measured based on such characteristics, for example, as inhibition of tumor growth, reduction of tumor mass or rate of growth, lack of detectable tumor associated antigens, and any other diagnostic measurement tool that is known in the field. Pharmaceutical efficacy can also be measured based on such characteristics, for example, as inhibition of the HIV virus and/or reduction and eradication of AIDS related symptoms. Moreover, pharmaceutical efficacy can also be measured based upon the reduction of the onset of symptoms that are related to the induction of organophosphorus nerve agent intoxication.

By "pharmaceutically effective amount" as used herein refers to the amount of an agent, reagent, compound, composition, or combination of reagents disclosed herein that when administered to a mammal that are determined to be sufficiently effective against cancer that is the object of the treatment or HIV/AIDS. A pharmaceutically effective amount will be known to those skilled in the art.

By the term "tumor" is meant to include both benign and malignant growths or cancer. The term "cancer," is meant to encompass, unless otherwise stated, both benign and malignant growths. In preferred aspects of the invention the tumor referred to is malignant. The tumor can be a solid tissue tumor such as a melanoma, or a soft tissue tumor such as a lymphoma, a leukemia, or a bone cancer. By the term "primary tumor" is meant the original neoplasm and not a metastatic lesion located in another tissue or organ in the patient's body. By the terms "metastatic disease," "metastases," and "metastatic lesion" are meant a group of cells which have migrated to a site distant relative to the primary tumor.

By "AIDS" is meant HIV infection: AIDS, ARC (AIDS related complex), both symptomatic and asymptomatic, and actual or potential exposure to HIV. Accordingly, the treatment of AIDS refers to the inhibition of HIV virus, the prophylaxis or treatment of infection by HIV and the prophylaxis, treatment or the delay in the onset of consequent pathological conditions such as AIDS. The prophylaxis of AIDS, treating AIDS, delaying the onset of AIDS, the prophylaxis of infection by HIV, or treating infection by HIV is defined as including, but not limited to, treatment of a wide range of states of HIV infection: AIDS, ARC (AIDS related complex), both symptomatic and asymptomatic, and actual or potential exposure to HIV.

The term "nicotinic acetylcholine receptor" refers to the endogenous acetylcholine receptor having binding sites for acetylcholine which also bind to nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

EXAMPLES

Example 1

The structures of Compound 1 and 2 were confirmed by UPLC-HRMS and found to have purities of 98% and 97%. Several analogs of Compounds 1 and 2, with different substitutions at positions of R1, R2, R3, and R4, were identified by substructure searches or chemical synthesis (Tables 1 and 2). Structure-activity relationships (SARs) were developed for both compounds using the binding assay. For example, substitution (e.g., methyl and chlorine) at R3 is tolerated for analogs of Compound 1. Both benzyl (1i) and isobutyl (1k) at R1 were more favorable than the more flexible phenethyl (1d).

For analogs of Compound 2, a bulky benzyl group at R1 yielded more potent receptor binding than a less bulky methyl or free base (2 vs 2h and 2i). More hydrophobic substitutions at R3 improved receptor binding (2f vs 2h). The R4 position tolerated different substitutions (e.g., hydrogen and halogen).

TABLE 1

| $R^1$ | $R^2$ | $R^3$ | Percent inhibition at 10 μM$^a$ (mean ± SD) |
|---|---|---|---|
| Benzyl | H | 3-Cl | 83.0 ± 1.7 |
| Benzyl | H | 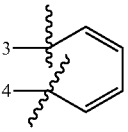 | 70.5 ± 3.1 |

TABLE 1-continued

| $R^1$ | $R^2$ | $R^3$ | Percent inhibition at 10 μM$^a$ (mean ± SD) |
|---|---|---|---|
| Phenethyl | H | 4-OMe | 9.5 ± 3.7 |
| 2-Methoxyethyl | H | 4-Cl | 27.3 ± 0.7 |
| Phenethyl | H | 2-Cl | 23.4 ± 2.4 |
| Isobutyl | Methyl | 2,5-F,F | 59.2 ± 0.2 |
| Phenethyl | H | 4-Cl | 18.3 ± 1.3 |
| Cyclopentyl | H | 2-Cl | 21.6 ± 2.6 |
| 2-Methoxyethyl | Methyl | 2-Cl | 43.0 ± 0.0 |
| Benzyl | Methyl | 2-Cl | 79.7 ± 1.9 |
| Phenethyl | H | 2-Me | 25.2 ± 1.8 |
| Isobutyl | Methyl | 2-Cl | 72.3 ± 1.0 |

Table 1 of Example 1 details binding affinity of nicotinic acetylcholine receptor antagonists, determined by radiolabeled binding, according to Formula I for the native α7 nAChR in rat brain membranes at 10 μM. Nicotinic acetylcholine receptor antagonists according to Formula I are listed as follows (from top to bottom): Compound 1, Compound 1a, Compound 1b, Compound 1c, Compound 1 d, Compound 1e, Compound 1 f, Compound 1 g, Compound 1h, Compound 1i, Compound 1j, and Compound 1k.

The binding affinity of these compounds for the native α7 nAChR in rat brain membranes was measured at 10 μM using [$^{125}$I] α-BTX as the radioligand. Non-Specific binding was determined with 1 μM MLA.

TABLE 2

| $R^1$ | $R^2$ | $R^3$ | $R^4$ | Percent inhibition at 10 μM$^a$ (Mean ± SD) |
|---|---|---|---|---|
| Benzyl | H | Propyl | H | 83.8 ± 2.3 |
| Benzyl | H | Methyl | 4-F | 50.0 ± 2.0 |
| Benzyl | H | Methyl | 4-Cl | 64.1 ± 1.8 |
| Methyl | Methyl | Methyl | 4-F | 11.9 ± 2.3 |
| Methyl | Methyl | Methyl | 4-Cl | 13.5 ± 5.3 |
| Methyl | Methyl | Cyclopropyl | 2-Furyl | 10.5 ± 1.7 |
| Methyl | H | 4-Tolyl | H | 23.4 ± 0.8 |
| Methyl | Methyl | 4-Tolyl | H | 12.1 ± 1.3 |
| Methyl | H | Propyl | H | 3.1 ± 0.1 |
| H | H | Propyl | H | 1.0 ± 2.8 |

Table 2 details binding affinity of nicotinic acetylcholine receptor antagonists, determined by radiolabeled binding, according to Formula II for the native α7 nAChR in rat brain membranes at 10 μM. Nicotinic acetylcholine receptor antagonists according to Formula II are listed as follows (from top to bottom): Compound 2, Compound 2a, Compound 2b, Compound 2c, Compound 2d, Compound 2e, Compound 2f, Compound 2g, Compound 2h, and Compound 2i.

The binding affinity of these compounds for the native α7 nAChR in rat brain membranes was measured at 10 μM using [$^{125}$I] α-BTX as the radioligand. Non-Specific binding was determined with 1 μM MLA.

Example 3

Binding assay was performed according to the previously reported method noted in Meyer, E. M.; Kuryatov, A.; Gerzanich, V.; Lindstrom, J.; Papke, R. L. J. Pharmacol. Exp. Ther. 1998, 287, 918. using [125I]a-BTX as the radioligand. 28 IC50 of Compound 1=1.6 1M; IC50 of Compound 8=2.9 1V. Dose-response curves of compounds 1 and 2 on the native neuronal α7 nAChR in rat brain membranes. The error bars indicate the standard deviation of the measurements. FIG. 1 details a representative dose response curves of Compound 1 and Compound 2 on the native neuronal alpha-7 nAChR in rat brain membranes. The line containing square-point designations indicates percent inhibition results regarding Compound 1, while the line containing triangle-point designations indicates the results regarding Compound 2.

Example 4

Figure 2:
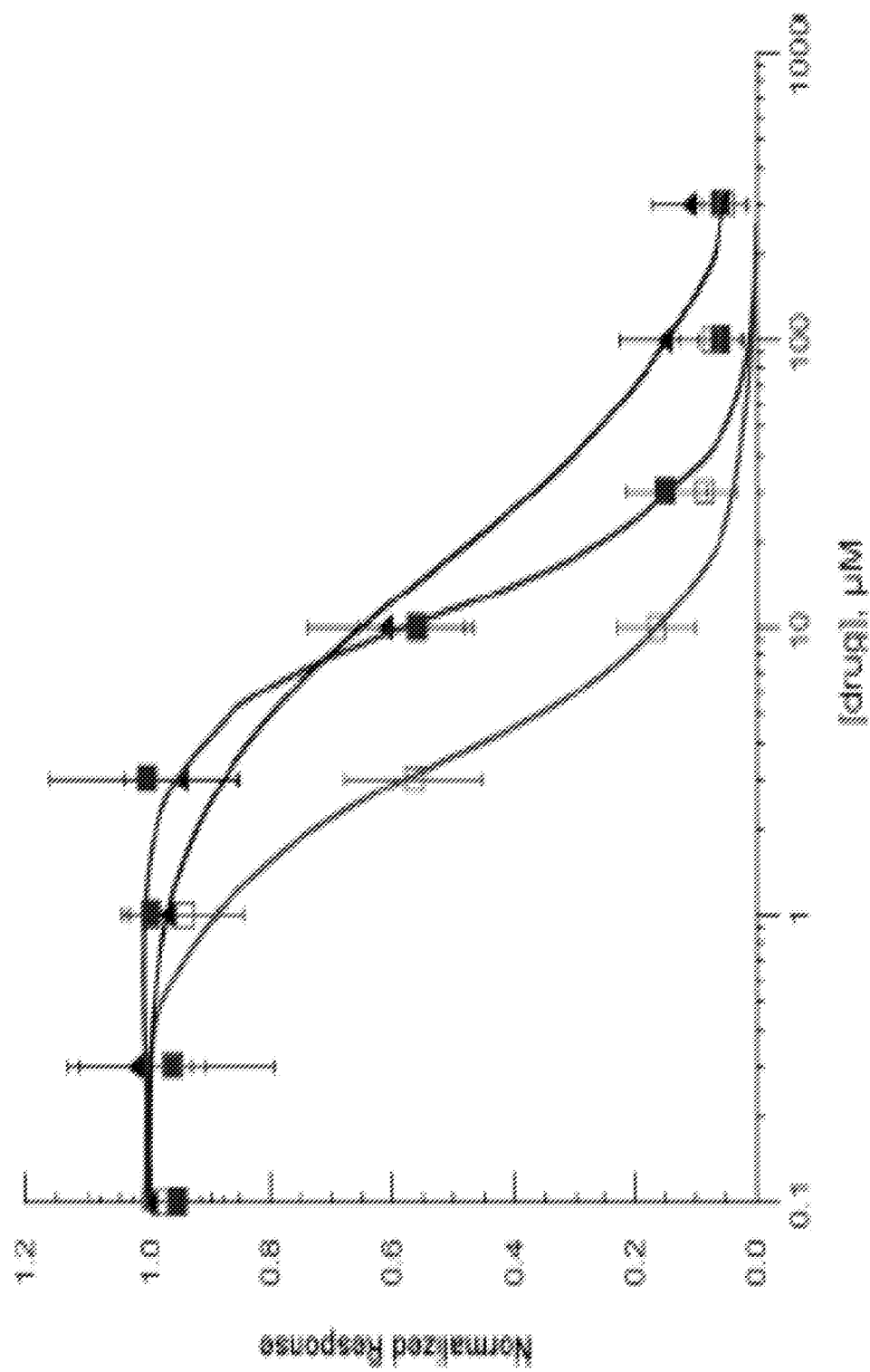
FIG. 2 is a depiction of the inhibition of human α7 AChR responses expressed in *Xenopus* oocytes.

The functional activity of compounds 1, 1i, and 2 is determined by electrophysical experiments on *Xenopus* oocytes expressing human alpha-7 nAChR. Human alpha-7 nAChR may be expressed in *Xenopus* oocytes by any means to known in the field. These three compounds are found to inhibit acetylcholine-evoked receptor responses in a dose-dependent manner, suggesting the subject compounds are $\alpha 7$ nAChR antagonists. The IC50 values of 1, 1i, and 2 are 11.9 µM, 3.7 µM, 18.9 µM, respectively. The $\alpha 7$ functional potency was 6-8 fold lower than the affinity estimated from human $\alpha 7$ receptor binding, and this difference may come from inter-species variation (rat vs. human), or variability in receptors (native vs. recombinant), or due to technical aspect of the functional assay in the oocyte expression system. FIG. 2 illustrates the inhibition of human $\alpha 7$ AChR responses expressed in *Xenopus* oocytes. The line containing solid square-point designations indicates percent inhibition results regarding Compound 1, while the line containing triangle-point designations indicates the results regarding Compound 2. The line containing hollow square-point designations indicates results regarding Compound 1i.

Example 5

Figure 3:
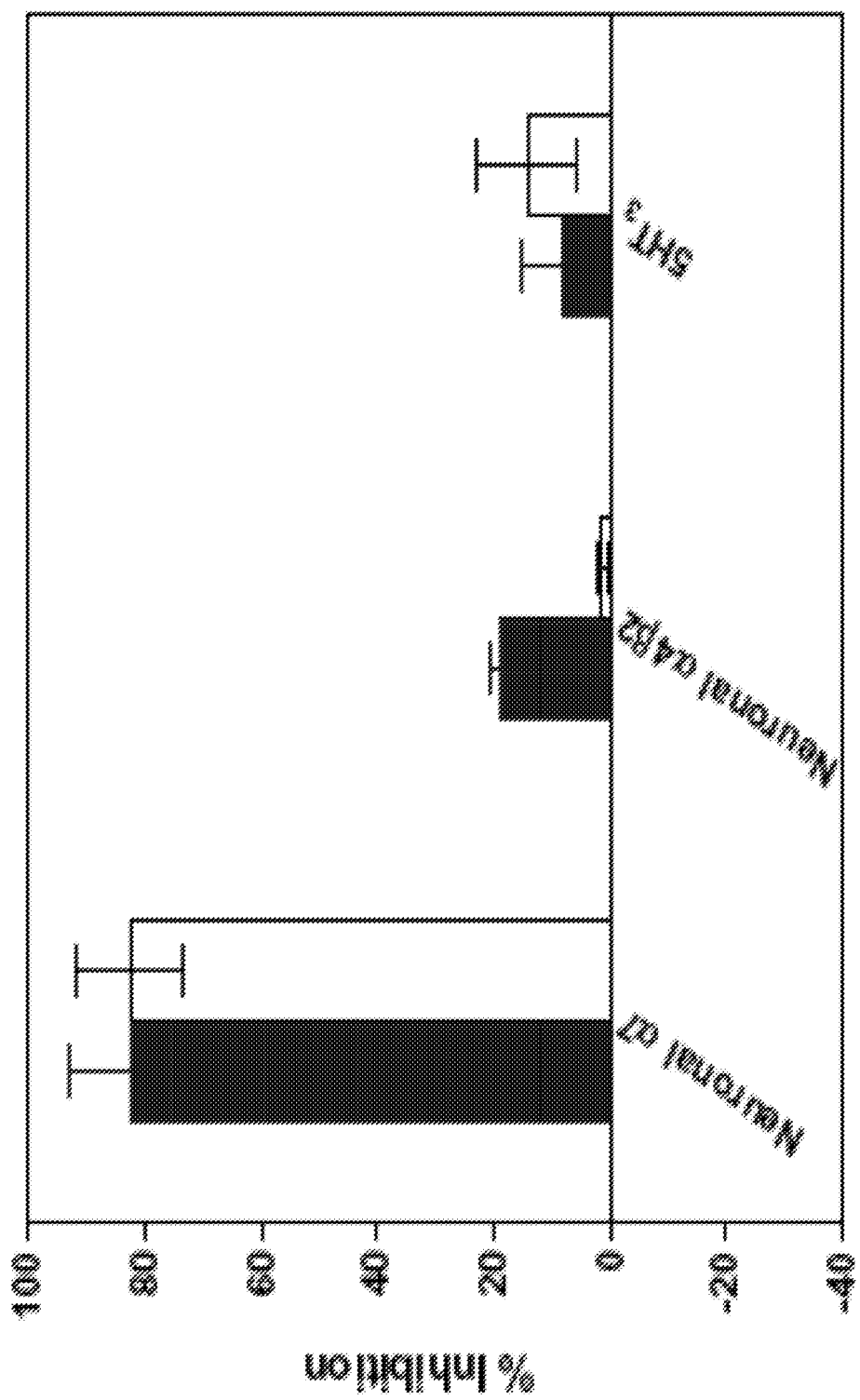
FIG. 3 is a depiction of the binding selectivity of Compound 1 and Compound 2.

The binding selectivity of Compound 1 and Compound 2 can be seen in FIG. 3. Compound 1 is represented by the solid bar while Compound 2 is represented by the empty bar. The selectivity of compounds 1 and 2 were measured using previously reported methods on three other receptors: neuronal $\alpha 4\beta 2$ nAChRs, muscle-type nAChRs, and $5HT_3$ receptors. The binding affinity for the $\alpha 4\beta 2$ receptor was performed on rat cortical membranes using [$^3$H]epibatidine as the radioligand. The muscle-type nAChR binding was determined using human TE671 cells with [$^{125}$I] $\alpha$-BTX as the radioligand. $5HT_3$ binding was measured on recombinant CHO cells expressing human $5HT_3$ receptor using [$^3$H]BRL 43694 as the radioligand. The orthosteric binding sites of the $\alpha 7$ nAChR and the 5HT3 receptor share a high degree of homology, therefore ligands for $\alpha 7$ nAChR and 5HT3 ligands frequently exhibit cross-activity. At 10 1M, compound 1 exhibited 82.5% binding to the $\alpha 7$ receptor and 18.8% and 8.4% binding to the neuronal $\alpha 4\beta 2$ and the $5HT_3$ receptor, respectively. Similarly, compound 2 showed binding affinities of 82.5% to $\alpha 7$, 1.3% to $\alpha 4\beta 2$, and 14.3% to $5HT_3$. Meanwhile, both compounds exhibited no detectable binding to the muscle-type nAChR at 10 µM. Taken together, these results demonstrated the selectivity of compounds 1 and 2 for the $5HT_3$ receptor over $\alpha 4\beta 2$, muscle-type nicotinic, and 5HT3 receptors The selectivity of compounds 1 and 2 was performed using methods previously discussed in Hope, A. G.; Peters, J. A.; Brown, A. M.; Lambert, J. J.; Blackburn, T. P. Br. J. Pharmacol. 1996, 118, 1237; Lukas, R. J. J. Neurochem. 1986, 46, 1936; Perry, D. C.; Kellar, K. J. J. Pharmacol. Exp. Ther. 1995, 275, 1030.

Example 6

Figure 4A:
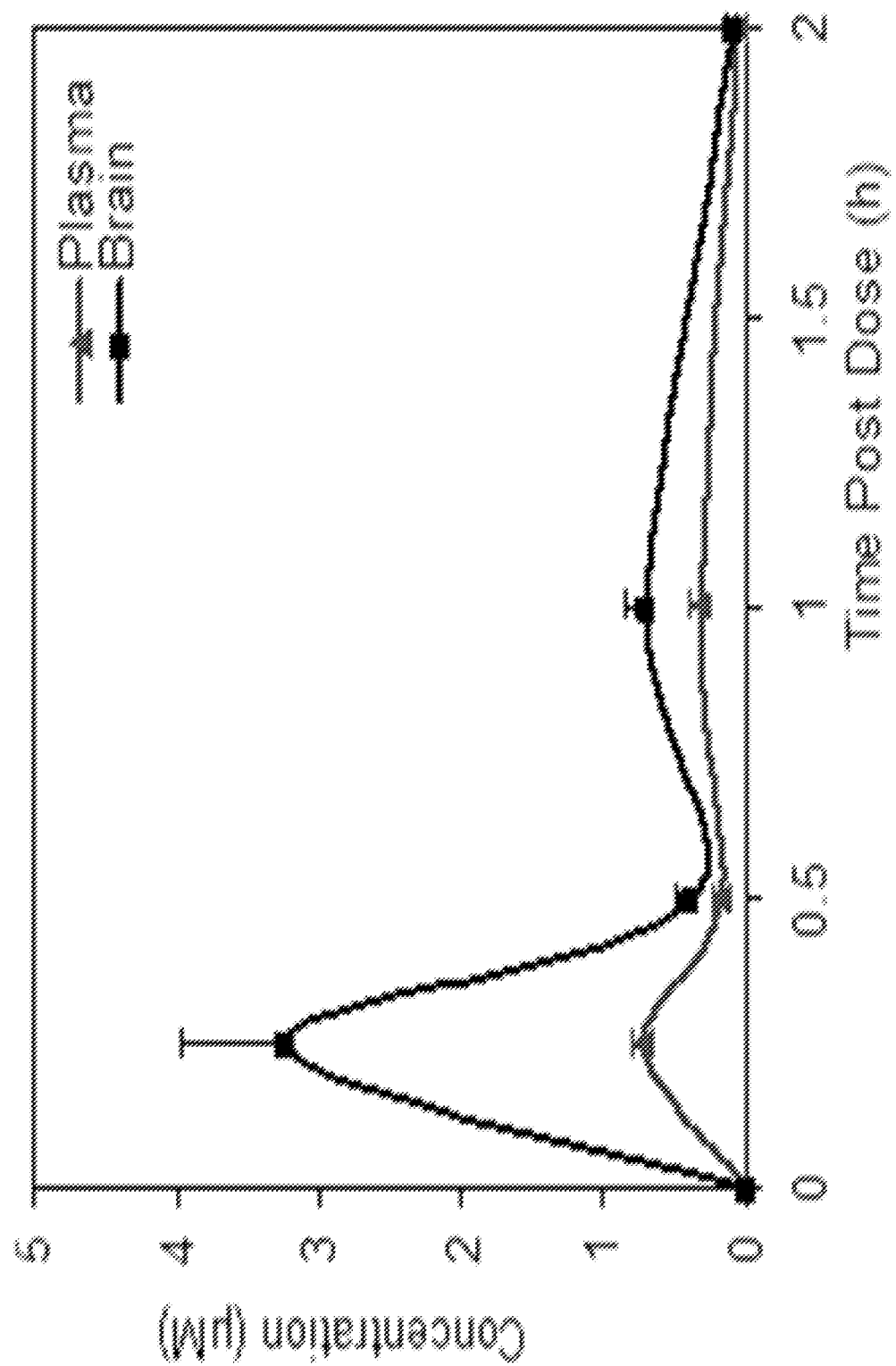
FIG. 4a and FIG. 4b depict brain and plasma concentrations for Compounds 1 and 2, respectively.
Figure 4B:
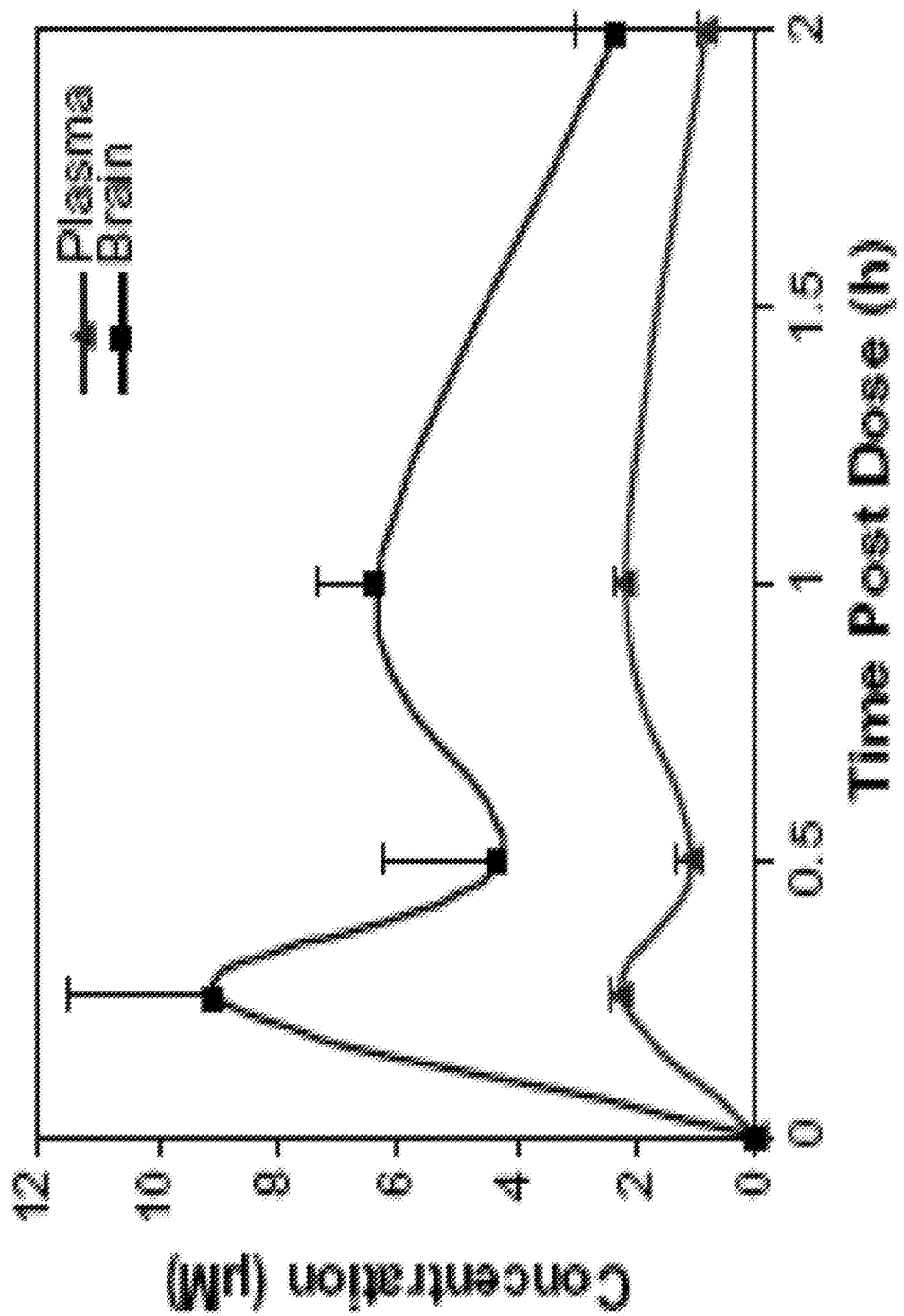

Compounds 1i and Compound 2 were tested in male C57Bl/6 mice (n≥3 per time point) for blood brain barrier after cassette dosing at 10 mg/kg via intraperitoneal (ip) administration. Brain and blood samples were collected at specific time points after drug administration. The area under the curve (AUC) ratios of brain to plasma were 2.8 and 3.1 for Compound 1i (FIG. 4*a*) and Compound 2 (FIG. 4*b*), respectively, suggesting good brain penetration for both compounds. Compound 2 achieved high concentration in brain (9 µM). Cassette dosing of compounds can lead to incorrect estimates of plasma drug levels by drug-drug interactions such as at the level of Cytochrome P450 enzymes or by interfering with transporter systems. Without being bound by theory, the biphasic nature of the drug plasma and brain levels would suggest some type of secondary uptake mechanism as is seen for drugs that are eliminated from the blood in part by the bile system and therefore available in the intestine to be taken up into the circulation a second time.

Example 7

| Seizure score (mean ± SD) | Normalized % seizure | Normalized % neuroprotection |
|---|---|---|
| 0 ± 0 | 0 | 100 |
| 9.1 ± 6.4 | 100 | 0 |
| 0.6 ± 1.3 | 6.6 | 93.4 |
| 0.8 ± 1.3 | 8.8 | 91.2 |

The table of Example 7 illustrates the neuroprotective activities of Compound 1i and Compound 2 against seizure induced by the nerve agent diisopropylfluorophosphate (DFP). The acetylcholine receptors (AChRs) are activated by acetylcholine (ACh), which is hydrolyzed to choline by acetylcholineesterase (AChE). When AChE is irreversibly inhibited by organophosphorus nerve agents like DFP and sarin, the uncontrolled accumulation of ACh at peripheral and central muscarinic AChRs (mAChRs) and nAChRs causes the cholinergic syndrome. This syndrome is characterized by sweating, pupillary constriction, convulsions, tachycardia, and eventually death. The mainstay treatment for nerve agent intoxication is the mAChR antagonist atropine together with an oxime reactivator of AChE (e.g., pralidoxime). This treatment regimen does not directly target nicotinic receptors although both mAChRs and nAChRs are involved in nerve agent toxicity. In this study, the new nAChR antagonists, Compounds 1i and 2 were tested in a DFP toxicity animal model to investigate their anti-seizure activity. Compared with the DFP controls, pretreatment with Compounds 1i and 2 antagonized DFP-induced seizure-like behaviors over a 2 h period post-injection by 93.4% and 91.2%, respectively. The results suggest that these compounds could provide neuroprotection against seizure-like behaviors induced by DFP and, therefore, may be useful for treatment of organophosphus nerve agent intoxication.

In summary, pharmacophore-based virtual screening led to the discovery of novel $\alpha 7$ nAChR ligands. A battery of property and functional group filters were applied to eliminate non-drug-like molecules and to reduce false positives. Two distinct families of small molecules (e.g., Compounds 1i and 2) were identified as novel $\alpha 7$ nAChR antagonists with selectivity for the neuronal $\alpha 7$ subtype over other nAChRs and good brain penetration. Neuroprotection against the seizure-like behaviors induced by DFP were observed for these compounds in a mouse model. The compounds should be very useful in discerning the physiological roles of neuronal $\alpha 7$ nAChR under normal and diseased states, and in discovering potential therapies for organophosphorus nerve agent intoxication.

Example 8

Figure 5:
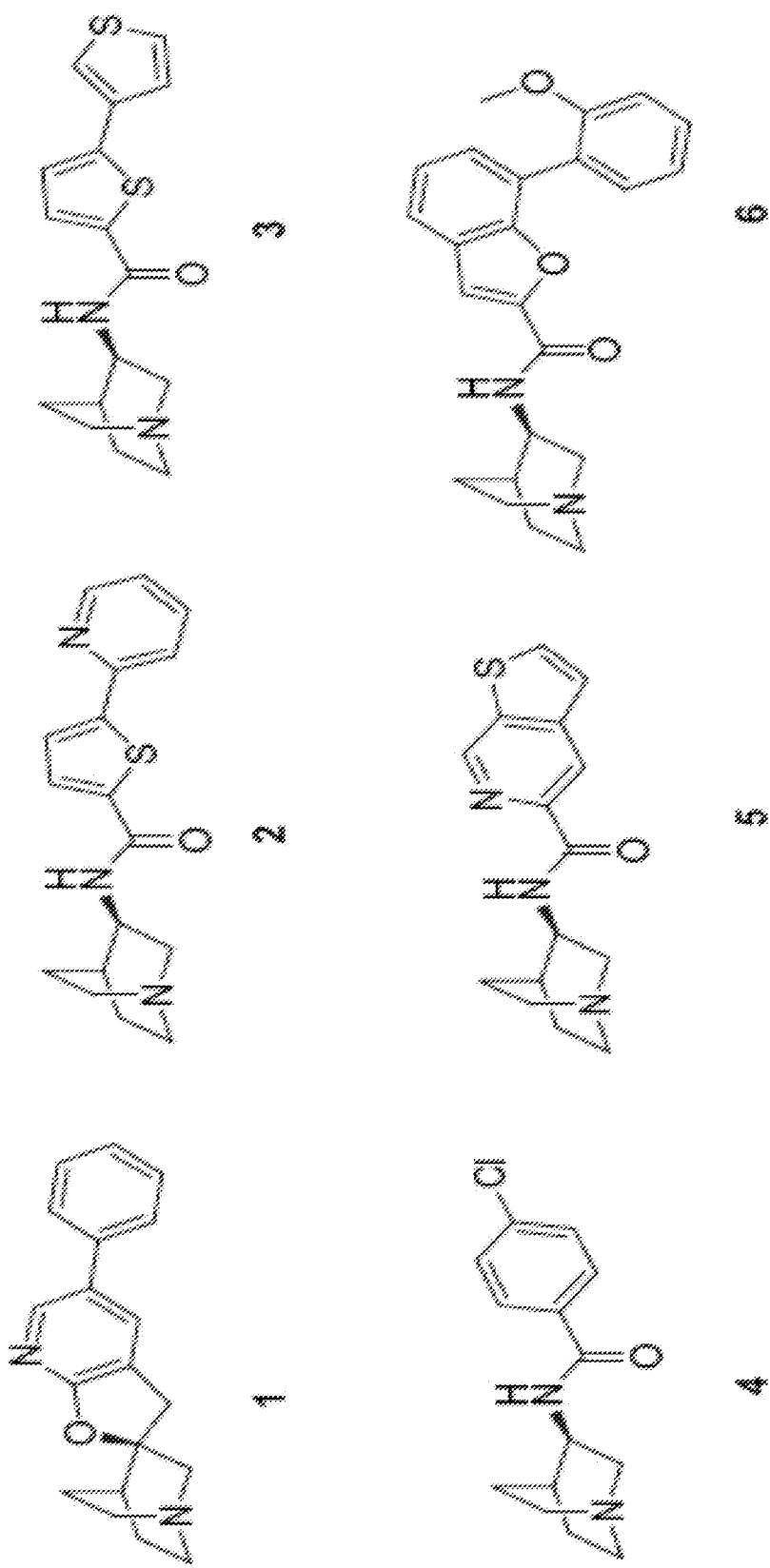
FIG. 5 demonstrates the alpha-7 selective ligands that may be used for pharmacophore development.

FIG. 5 demonstrates the alpha-7 selective ligands that may be used for pharmacophore development.

Three dimensional (3D) pharmacophore models may be developed and, subsequently conducted ligand-based virtual screening may also be conducted to search for novel α7 nAChR selective ligands. Here, six potent and selective α7 ligands are representative of a selected training set for the pharmacophore model. The structures of all compounds could be protonated at physiological conditions (pH 7.4). Flexible structural alignments may be performed to identify the common chemical features responsible for the α7 receptor binding using the Flexible Alignment module within MOE. This alignment method uses a stochastic search algorithm to simultaneously explore the conformation space of all compounds in the training set.

Figure 6:
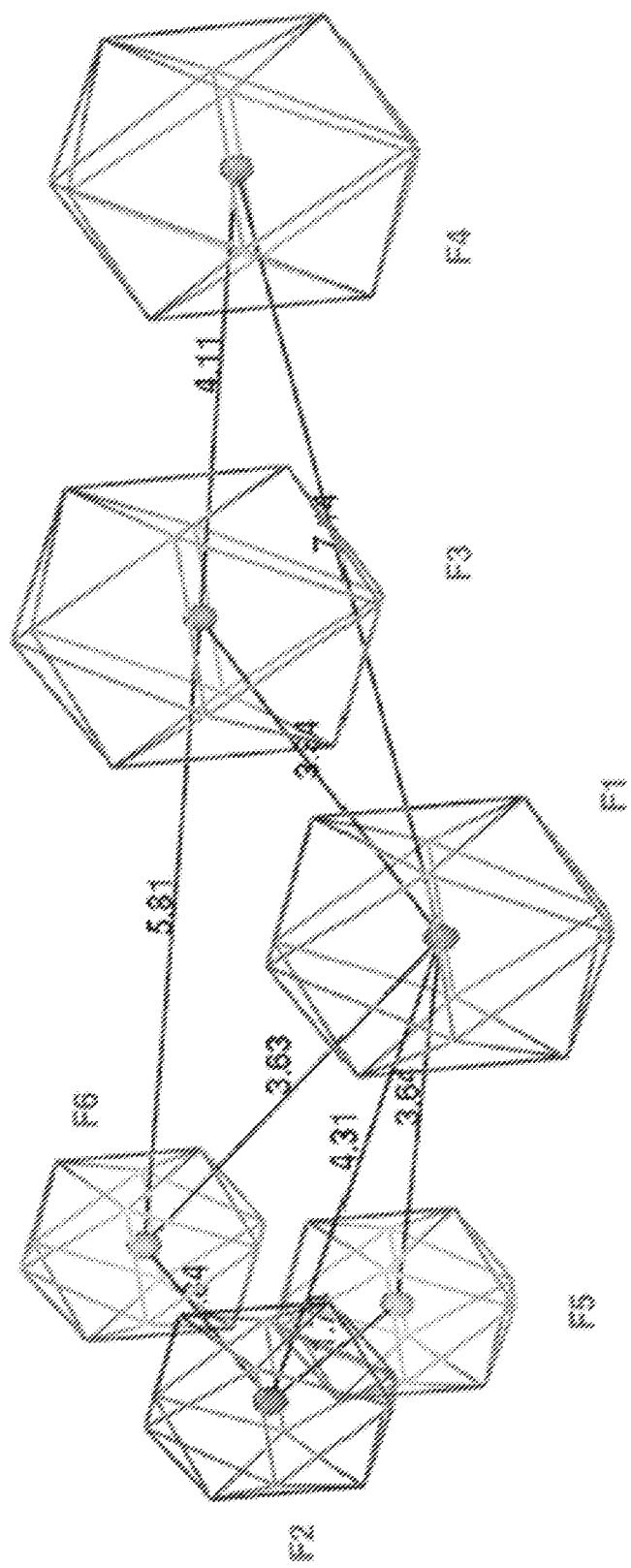
FIG. 6 depicts a six-point pharmacophore model may be obtained based on the unified scheme within MOE.

This operation generates several scores to quantify the quality of each alignment with lower scores indicating better alignments. The alignments with the lowest S score may be selected for the 3D pharmacophore development. A six-point pharmacophore model may be obtained based on the unified scheme within MOE (FIG. 6). Feature F1 is a hydrogen bond acceptor with radius 1.5 Å. Feature F2 is a cation atom (radius: 1 Å)—the basic nitrogen, which exists in most known nAChR ligands. Features F3 and F4 are characterized as aromatic rings with radius 1.5 Å. Features F5 and F6 cover hydrophobic regions (radius: 1.0 Å). The pharmacophore model may be used to screen compounds assembled from different sources. In order to remove unwanted structures and accelerate the process of virtual screening, extended Lipinski's rules 22 and three functional group filters were applied before the pharmacophore-based database searching. Extended Lipinski's rules include seven filters: 100<molecular weight≤500_2≤Clog P≤5, number of hydrogen bond donors≤5, number of hydrogen bond acceptors≤10, topological polar surface area≤120 A2, number of rings≤5, and number of rotable bonds≤10. These property filters may be chosen to eliminate compounds that lacked sufficient drug-like properties to become drugs. Compounds that passed the above criteria are subjected to three functional group filters: absence of reactive groups, number of non-fluorine halogen atoms≤4, and number of basic nitrogen atoms P1. Reactive groups are defined according to the Oprea set, including heteroatom-heteroatom single bonds, acyl halides, sulfonyl halides, per-halo ketone, and Michael acceptors. These groups can interfere with high-throughput biochemical screening assays and therefore often appear as false positives. A halogen filter may be used to avoid pesticides that often contain a nitrogen atom protonated at physiological conditions (pH 7.4) and this nitrogen atom has been shown to be involved in extensive cation-p interactions between ligand and receptor.

A basic nitrogen filter may be selected to remove compounds that lack this chemical feature. This filter greatly reduced the size of the compound database and therefore improved the speed of conformer generation and pharmacophore matching. Altogether, compounds violating P2 Lipinski's rules or any functional group filters were eliminated from our selection. The resulting compounds are subjected to conformation sampling using the Conformational Import Module, a high throughput method to generate 3D low-energy conformers in MOE. Recent studies revealed that this method performed as well as the established Catalyst FAST module. The ensemble of conformers were then screened by the six-point pharmacophore model by enabling exact match of features F1-F4 and partial match of features F5 and F6. The consequent hits were subjected to database diversity and clustering analyses with the aim to remove close analogs and maximize the chemotypes of the selected compounds for biological tests. The MDL MACCS fingerprints implemented in MOE are calculated for all compounds and fingerprints-based clustering may be carried out by using the Tanimoto coefficient (0.85) as a measure of fingerprint similarity. No more than three representative compounds in the same cluster are selected for the final collection.

About 300 compounds are acquired from different commercial sources for in vitro biological screening, including compounds from Maybridge, Chembridge, Enamine. The binding affinity of these compounds for the native α7 nAChR in rat brain membranes are measured using methods known in the art, particularly with [125I] α-BTX as the radioligand. From the preliminary screening, various chemotypes are found to exhibit P50% inhibition on the α7 nAChR in this assay. Two of them (compound 1 and 2, Tables 1 and 2 in Examples 1 and 2 disclosed herein) exhibit low micromolar inhibition on brain α7 nAChR with an IC50 of 1.6 μM and 2.9 μM, respectively (FIG. 3). The structures of 1 and 2 are confirmed by UPLC-HRMS and found to have purities of 98% and 97%. Several analogs of 1 and 2 with different substitutions at positions of R1, R2, R3, and R4 are identified by substructure searches or chemical synthesis (Tables 1 and 2 in examples 1 and 2 disclosed herein). Structure-activity relationships (SARs) are developed for both compounds using the binding assay. For example, substitution (e.g. methyl and chlorine) at R3 is tolerated for analogs of compound 1. Both benzyl (1i) and isobutyl (1K) at R1 were more favorable than the more flexible phenethyl (1d). For analogs of compound 2, a bulky benzyl group at R1 yielded more potent receptor binding than a less bulky methyl or free base (2 vs 2h and 2i). More hydrophobic substitutions at R3 improved receptor binding (2f vs 2h). The R4 position tolerated different substitutions (e.g. hydrogen and halogen).

Details of Examples 1-8 are disclosed in Peng et al., "Discovery of novel α7 nicotinic receptor antagonists" Bioorganic & Medicinal Chemistry Letters 20 (2010) 4825-4830, the contents of which are incorporated herein by reference in its entirety.

Example 9

Animals were housed in individual standard cages on sawdust bedding in an air-conditioned room (about 20° C.). They were kept under a 12/12 h light/dark cycle (lights on from 19.00 to 07.00) and had free access to food and water. Rats were housed and tested in the same room. A radio, which was playing softly, provided background noise in the room. All testing was done between 09.00 and 17.00 hours.

Figure 7A:
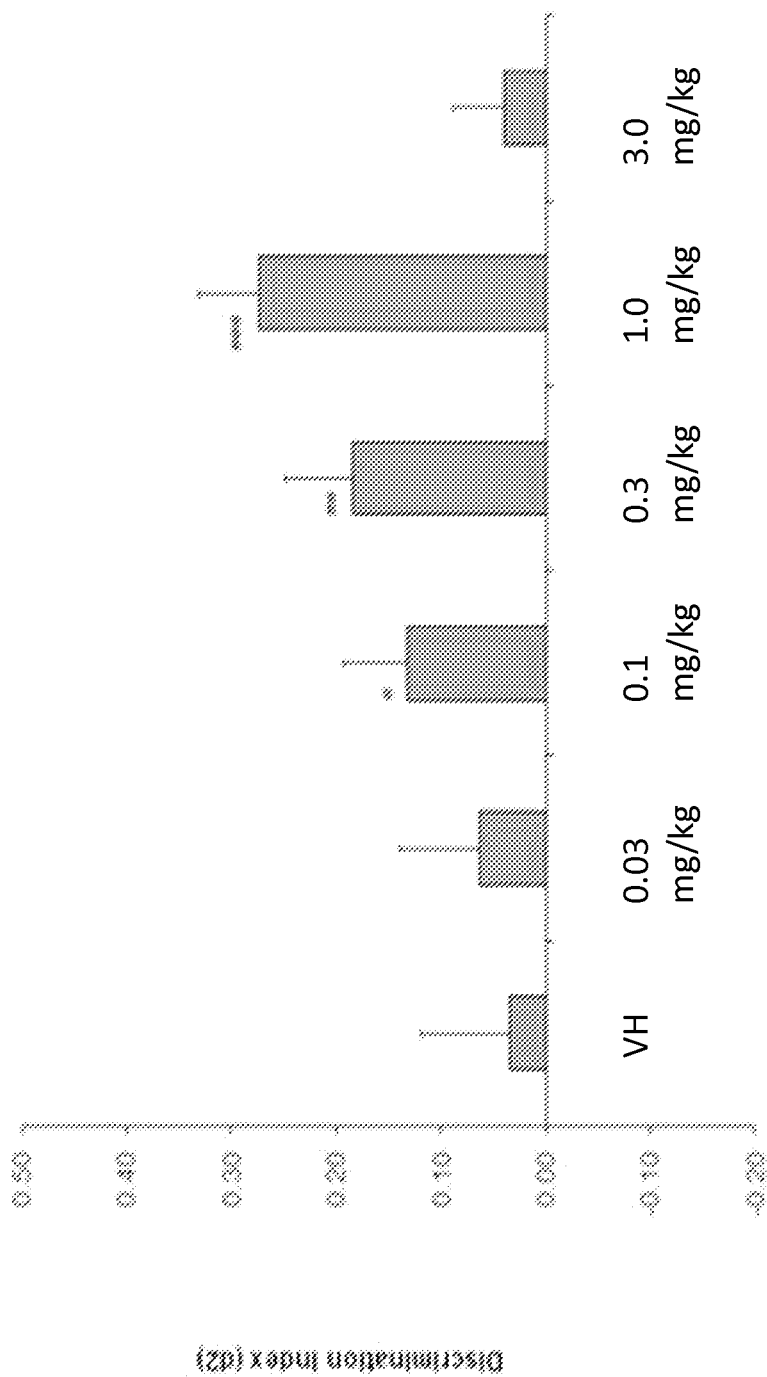
FIG. 7a depicts the results of the Novel Object Recognition test wherein the compound was administered 15 min prior to the first trial.

Compound 1i was tested at 0, 0.3, 1, and 3 mg/kg in a time-dependent memory deficit model, i.e. a 24 h inter-trial interval (See, FIG. 7a). Compound 1i was administered by intraperitoneal injection (i.p. injection), 15 minutes before the first trial. The order of the treatments was balanced to prevent the data from being distorted by potential object- and side-preferences of the animals.

The object recognition test was performed as described elsewhere (e.g., Ennaceur and Delacour, 1988). The apparatus consisted of a circular arena, 83 cm in diameter. The back-half of the 40 cm high arena wall was made of gray polyvinyl chloride, the front-half consisted of transparent polyvinyl chloride. The light intensity was equal in the different parts of the apparatus, as fluorescent red tubes provided a constant illumination of about 20 lux on the floor of the apparatus. Two objects were placed in a symmetrical position at about 10 cm from the wall, on a diameter from the left- to the right-side of the arena. Each object was available in triplicate. Four different sets of objects were used. The different objects were: 1) a cone consisting of a gray polyvinyl chloride base (maximal diameter 18 cm) with a collar on top made of aluminum (total height 16 cm), 2) a standard 1 L transparent glass bottle (diameter 10 cm, height 22 cm) filled with water, 3) a massive metal cube (10.0×5.0×7.5 cm) with two holes (diameter 1.9 cm), and 4) a solid aluminum cube with a tapering top (13.0×8.0×8.0 cm). Rats were unable to displace the objects.

A testing session consisted of two trials. The duration of each trial was 3 min. During the first trial (T1) the apparatus contained two identical objects (samples). Rats were placed in the apparatus facing the wall at the middle of the front (transparent) segment. After the first exploration period the rat was put back in its home cage. Subsequently, after a 24 h delay interval, the rat was put in the apparatus for the second trial (T2). The total time an animal spent exploring each object during T1 and T2 was recorded manually with a personal computer.

Exploration was defined as follows: directing the nose to the object at a distance of no more than 2 cm and/or touching the object with the nose. Sitting on the object was not considered as exploratory behavior. A minimal amount of object interaction is required in order to achieve reliable object discrimination, therefore rats that explored less than 7 s in T1 and/or 9 s in T2 were excluded from the analyses. In order to avoid the presence of olfactory cues the objects were always thoroughly cleaned after each trial. All object combinations as well as the location (left or right) of the novel object were used in a balanced manner to avoid potential biases due to preferences for particular locations or objects.

In several studies it was shown that Wistar rats show a good object memory performance when a 1 h delay is interposed between the first trial and the second trial. However, when a 24 h delay is used rats do not discriminate between the novel and the familiar object in the second trial, indicating that the rats do not remember the object that was presented in the first trial. Using a 6 h delay, the discrimination performance is in-between than of the 1 h and 24 h delays, suggesting a delay-dependent forgetting in this task. In the first two weeks, the animals were handled daily and were allowed to get accustomed to the test setup in two days, i.e. they were allowed to explore the apparatus (without any objects) twice for 3 min each day. Then the rats were adapted to the testing routine until they showed a stable discrimination performance, i.e. good discrimination at 1 h interval and no discrimination at twice for 3 min each day. Then the rats were adapted to the testing routine until they showed a stable discrimination performance, i.e. a good discrimination at 1 h interval and no discrimination at. In FIG. 5a, Compound 1i was injected i.p. 15 before T1 and a 24 h inter-trial interval was used.

The basic measures were the times spent by rats in exploring an object during T1 and T2. The time spent in exploring the two identical samples will be represented by 'a1' and 'a2'. The time spent in T2 in exploring the sample and new object will be represented by 'a' and 'b', respectively. The following variables were calculated: e1=a1+a2, e2=a+b, and d2=(b−a)/e2. E1 and e2 are measures of the total exploration time of both objects during T1 and T2 respectively. d2 is a relative measure of discrimination corrected for exploration activity in the test-trial (e2). Thus, even if a treatment would affect exploratory behavior the d2 index will be comparable between conditions.

As seen in FIG. 5a, the relative cognitive score (d2) showed a progressive increase up to 1.0 mg/kg of Compound 1i. There was no increase in cognition at administration of Compound 1i at doses of 3.0 mg/kg.

Example 10

Animals were housed, treated, and a Novel Object Recognition/Object Recognition Test was performed substantially similar to the methods and procedures described in Example 9.

One important difference, however, was that compound 1i was administered one hour after T1 in this example. The results of this test are depicted in FIG. 7b.

Figure 7B:
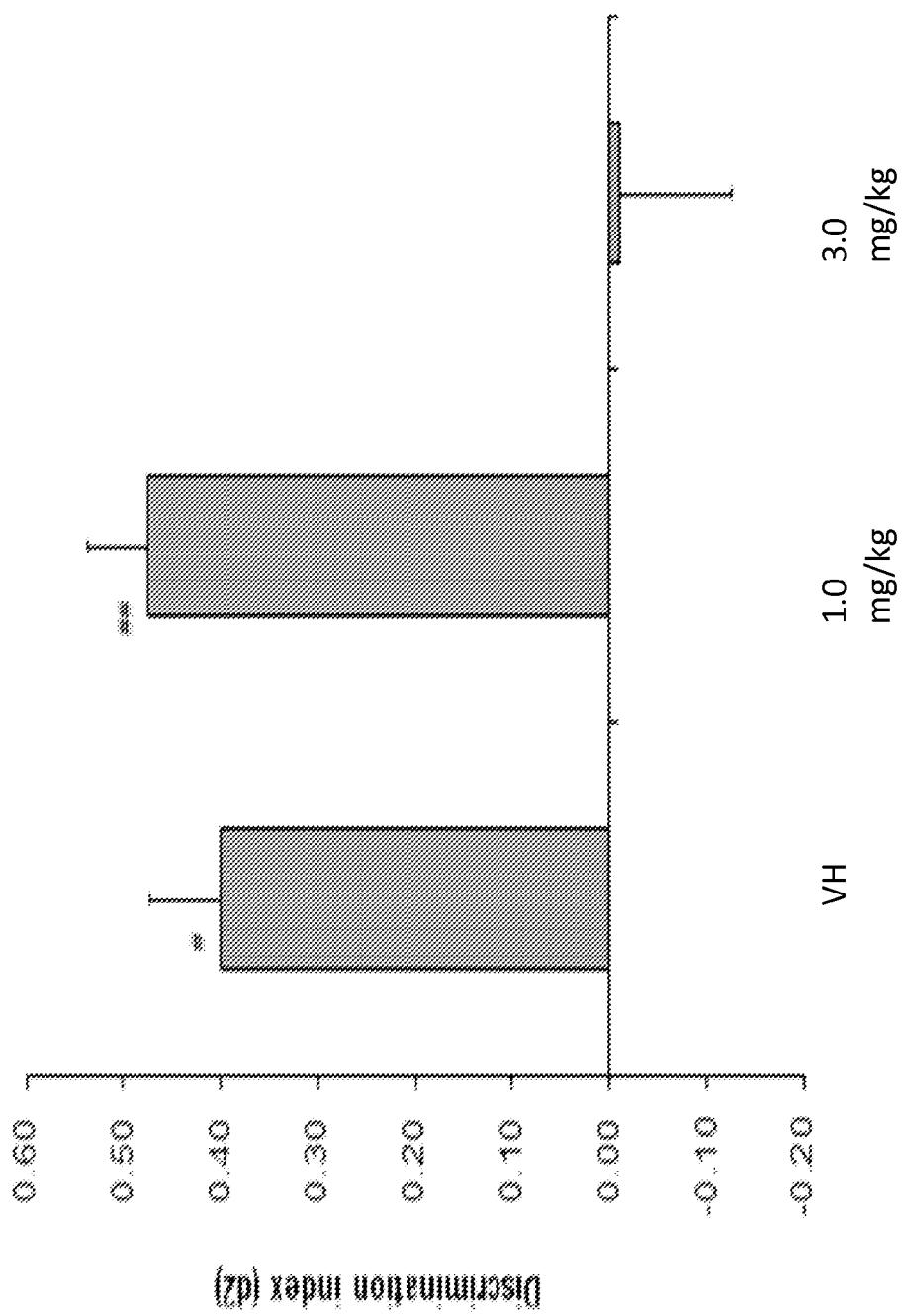
FIG. 7b depicts the results of the Novel Object Recognition test wherein the compound was administered 1 hour following the first trial.

As illustrated by FIG. 7b, administration of Compound 1i, at a dose of 1.0 mg/kg, post-T1 significantly enhances cognition in treated animals. However, dosages at about 3.0 mg/kg actually reduced cognition in animals that were treated with larger doses 1 hour post-T1. Without being bound by theory, this data, along with the data in FIG. 5a, suggests a theory wherein in certain circumstances administration of lower doses of alpha-7 nicotinic receptor antagonists disclosed herein (i.e. Compound 1i) may function to prevent desensitization of the nAChR and thereby possibly increase the efficacy of endogenous acetylcholine. Without being bound by theory, the duration of the compound administration may also possibly play an important role.

Example 11

Compounds listed in Tables 1 and 2, of Example 1, can be purchased Maybridge, Chembridge, Enamine. Details for procurement of these compounds is generally disclosed in Peng et al., "Discovery of novel α7 nicotinic receptor antagonists" Bioorganic & Medicinal Chemistry Letters 20 (2010) 4825-4830, the contents of which are disclosed herein by reference. General methods of synthesis are also disclosed in U.S. provisional application 61/501,207, the contents of which are disclosed herein by reference.

What is claimed:
1. A method for the treatment of a disease or disorder characterized by the activation of an acetylcholine receptor pathway, comprising administering to the patient an effective amount of a α7 nicotinic acetylcholine receptor antagonist according to Formula I or Formula II in a free or pharmaceutically acceptable salt form, wherein said disease or disorder is selected from the group consisting of small-cell lung cancer, non-small cell lung cancer, organophosphorus nerve agent intoxication, human immunodeficiency virus (HIV) infection, acquired immune deficiency syndrome (AIDS), squamous cell carcinoma, adenocarcinoma, large cell carcinoma, pleura mesothelioma, solid tumor carcinoma, cognitive impairment, or a combination thereof, or wherein treatment is directed towards improving cognition, or smoking cessation, wherein Formula I is:

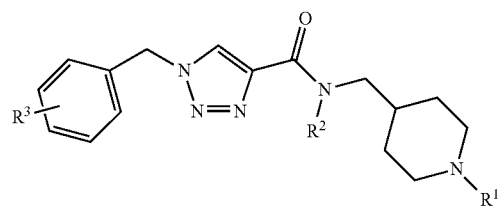

Wherein $R_1$ is selected from a benzyl, phenethyl, 2-methoxyethyl, isobutyl, or cyclopentyl group;
Wherein $R_2$ is selected from a hydrogen or methyl group;
Wherein $R_3$ is selected from a chlorine, methoxyethyl, methyl, fluorine or cyclopentyl group;

and Formula II is:

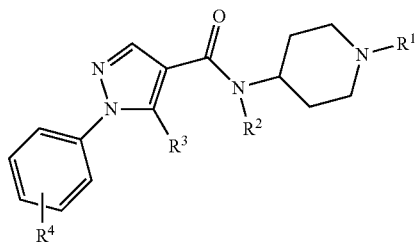

Wherein R₁ is selected from a benzyl, methyl, or hydrogen group;
Wherein R₂ is selected from H or methyl;
Wherein R₃ is selected from a propyl, methyl, cyclopropyl, or 4-tolyl group;
Wherein R₄ is selected from a hydrogen, fluorine, chlorine, or furyl group.

2. The method of claim 1, wherein said disease or disorder is small cell lung cancer.

3. The method of claim 1 wherein said disease or disorder is non-small cell lung cancer.

4. The method of claim 1, wherein said disease or disorder is organophosphorus nerve agent intoxication.

5. The method of claim 1 wherein said disease or disorder is infection via the human immunodeficiency virus (HIV).

6. The method of claim 1, wherein said disease or disorder is acquired immune deficiency syndrome (AIDS).

7. The method of claim 1, wherein said disease or disorder is selected from squamous cell carcinoma, adenocarcinoma, large cell carcinoma, or pleura mesothelioma.

8. The method of claim 1 wherein said disease or disorder is a solid tumor carcinoma.

9. The method of claim 1, wherein a novel α7 nicotinic acetylcholine receptor antagonist of Formula I is administered simultaneously with a second treatment for cancer selected from the group consisting of: capecitabine, trastuzumab, pertuzumab, cisplatin and irinotecan.

10. The method of claim 1, wherein the disease or disorder is a cognitive impairment.

11. The method of claim 10, wherein the cognitive impairment is selected from the group consisting of impaired auditory processing and attention, impaired spatial organization, impaired verbal learning, impaired semantic and verbal memory, impaired executive functions, or Alzheimer's disease.

12. The method of claim 1, wherein the disease or disorder is Alzheimer's disease.

13. The method of claim 1, wherein said disease or disorder is cognitive impairment, and said cognitive impairment is a symptom of Alzheimer's disease.

14. The method of claim 1, wherein the treatment is directed toward smoking cessation in a patient.

15. The method of claim 1, wherein said disease or disorder is cognitive impairment, and said cognitive impairment is a symptom of psychosis.

16. The method claim 1, wherein the treatment is directed toward improving cognition.

* * * * *